United States Patent
Cramail et al.

(10) Patent No.: US 9,133,305 B2
(45) Date of Patent: Sep. 15, 2015

(54) POLYURETHANE SYNTHESIS BY MEANS OF SELF-CONDENSATION

(75) Inventors: Henri Cramail, Pessac (FR); Aurelie Boyer, Bordeaux (FR); Dnyaneshwar Palaskar, Talence (FR); Eric Cloutet, Saint Caprais de Bordeaux (FR); Carine Alfos, Pessac (FR)

(73) Assignee: CENTRE NATIONAL DE LA RECHERCHE SCIENTIFIQUE (C.N.R.S.), Paris (FR)

( * ) Notice: Subject to any disclaimer, the term of this patent is extended or adjusted under 35 U.S.C. 154(b) by 372 days.

(21) Appl. No.: 13/502,284

(22) PCT Filed: Oct. 15, 2010

(86) PCT No.: PCT/FR2010/052190
§ 371 (c)(1),
(2), (4) Date: Jul. 6, 2012

(87) PCT Pub. No.: WO2011/045546
PCT Pub. Date: Apr. 21, 2011

(65) Prior Publication Data
US 2012/0264901 A1    Oct. 18, 2012

(30) Foreign Application Priority Data
Oct. 15, 2009 (FR) ...................................... 09 57223

(51) Int. Cl.
*C08G 71/04* (2006.01)
*C07C 247/22* (2006.01)

(52) U.S. Cl.
CPC .............. *C08G 71/04* (2013.01); *C07C 247/22* (2013.01)

(58) Field of Classification Search
USPC ...................................... 528/367, 368; 552/6
IPC .................................. C08G 71/04; C07C 247/22
See application file for complete search history.

(56) References Cited

U.S. PATENT DOCUMENTS 2,334,476 A * 11/1943 Coffman ........................ 560/355
2,764,599 A *  9/1956 Clifford et al. .................... 552/6
3,376,127 A *  4/1968 McConnell et al. ........... 504/151
3,725,450 A *  4/1973 Coury et al. .................... 560/343
2003/0065188 A1* 4/2003 Widdowson et al. ......... 546/308
2009/0270505 A1* 10/2009 Andjelkovic et al. ......... 514/563

OTHER PUBLICATIONS

Database Beilstein [Online], Widdowson et al., "2-Azidocarbonylpentane," *Beilstein Institute for Organic Chemistry*, Database accession No. 3030004 (2003).
Kumar et al., "A Novel One-pot Synthesis of Hyperbranched Polyurethanes," *J. Chem. Soc.*, ISSN: 0022-4936, 1453-1454 (1993).
Kumar et al., "Hyperbranched Polyurethanes with Varying Spacer Segments Between the Branching Points," *J. Polymer Science*, 34(5): 839-848 (1996).
Ranganathan et al., "Synthesis of New Hermotropic Liquid Crystalline Polyurethanes Containing Biphenyl Mesogens Using a Novel AB-type self-polycondensation," *Chem. Comm.*, 154-155 (2003).
Int'l Search Report issued in app. No. PCT/FR2010/052190 (2011).
Ghatge, N.D. and Jadhav, J.Y. 1983 Synthesis, characterization, and properties of novel poly(ether urethanes) *J Polymer Sci* 21: 1941-1950.

* cited by examiner

*Primary Examiner* — Rabon Sergent
(74) *Attorney, Agent, or Firm* — Knobbe, Martens, Olson & Bear, LLP

(57) ABSTRACT

The present invention relates to a compound with the following formula (I) where: $R_1$ is particularly a straight or branched alkyl group, a is a single or double bond; $R_2$ is particularly a hydrogen atom; $R_3$ and $R_5$ are a hydrogen atom when a is a single bond, and absent when a is a double bond; $R_4$ is a hydrogen atom or an $OR_b$ group, where $R_b$ is a hydrogen atom or an alkyl group including 1 to 12 atoms of carbon, and $A_1$ is a divalent alkylene radical.

21 Claims, 5 Drawing Sheets

POLYURETHANE SYNTHESIS BY MEANS OF SELF-CONDENSATION

CROSS REFERENCE TO RELATED APPLICATIONS

This application is a U.S. nationalization under 35 U.S.C. §371 of International Application No. PCT/FR2010/052190, filed Oct. 15, 2010, which claims priority to French application no. FR 0957223, filed Oct. 15, 2009. The disclosures set forth in the referenced applications are incorporated herein by reference in their entireties.

The subject of the present invention is the synthesis of polyurethane by self-condensation. A further subject concerns novel monomers, methods for preparing the same and the use thereof for polyurethane synthesis.

Polyurethanes are among the most important polymeric materials and have numerous useful properties for various applications, such as the machinery industry, coatings and coverings, paints, insulating materials, elastic fibres, flexible foam or medical devices. In addition, the chemistry of polyurethanes allows the synthesis of different types of polymer materials such as foam (flexible and rigid), thermoplastic materials, interpenetrating polymer networks (IPNs), and segmented polyurethanes in relation to the polyol, the isocyanate and the polymerisation method used.

Recently, there has been strong interest in the synthesis of polyurethanes from natural resources such as vegetable oils and natural fats on account of their large availability, durability and biodegradable nature. In addition, they have better ecological compatibility than petrochemical products. Numerous recent studies concern the synthesis and characterisation of a broad range of polymers from vegetable oils (Miyagawa, H.; Misra, M.; Drzala, L. T.; Mohanty, A. K. *Polymer*, 2005, 46, 445; Lu, Y.; Larock, R. C. *Biomacromolecules*, 2008, 9, 3332; Wang, H. J.; Rong, M. Z.; Zhang, M. Q.; Hu, J.; Chen, H. W.; Czigány, T. *Biomacromolecules* 2008, 9, 615).

Vegetable oils are triglycerides and most of the time they have at least one unsaturated fatty acid in their structure (Petrovic, Z. *Polymer Reviews*, 2008, 48, 109). The use of enzymes or chemical products to modify the structure of the fatty acid and to insert functional groups has long been known (Leitheiser, R. H.; Peloza, C. C.; Lyon, C., K. J. *Cellular Plastics* 1969, 5, 346; Ehrich, A.; Smith, M. K.; Patton, T. C. *J Am Oil Chem Soc*, 1959, 6, 149; Sakamoto, W. K.; Kanda, D. H. F.; Andrade, F. D. A.; Das-gupta, D. K. *J. Mater. Sci.*, 2003, 38, 1465; Fan, Q.; Xiao, C. Polymer Composite, 2008, 758; Alam, J.; Riaz, U.; Ahmad, S., *Polym. Adv. Technol.* 2008, 19, 882; Zanetti-Ramos, B. G.; Lemos-Senna, E.; Soldi, V.; Borsali, R.; Cloutet, E.; Cramail, H., *Polymer*, 2006, 47, 8080). Numerous types of vegetable oils have therefore been tested for the synthesis of polyols, such as rapeseed oil, tung oil, linseed oil, sunflower oil or soybean oil.

Polyurethanes are conventionally prepared by the reaction of polyols with isocyanates.

Isocyanates are highly reactive and chemically toxic. It is therefore desirable to use a method for preparing polyurethanes via a route that does not use isocyanates ("non-isocyanate" route).

Numerous studies have been conducted on the synthesis of novel polyols intended for the preparation of polyurethanes but not so many on the synthesis of polyurethanes from vegetable oils without the use of isocyanates.

At the present time there are two types of "non-isocyanate" routes. The first type is the self-condensation method in which a monomer of type AB contains hydroxyl and azide groups (Kumar, A.; Ramakrishnan, S. *Chem. Commun.*, 1993, 1453; Kumar, A.; Ramakrishnan, S. *J. Polym. Sci.: Part A Polym. Chem.*, 1996, 34, 839; Ranganathan, T.; Ramesh, C.; Kumar, A. *Chem. Commun.*, 2004, 154). The other type of method concerns the ring opening of cyclic carbonates using amines (Ochiai, B.; Satoh, Y.; Endo, T, J. *Polym. Sci. Part A: Polym Chem.*, 39, 4091, 2001).

It is therefore the objective of the present invention to provide a novel method for preparing polyurethane via a non-isocyanate route.

The objective of the present invention is to provide a method for preparing polyurethane in the absence of isocyanates, the said method allowing stoichiometric monitoring.

A further objective of the present invention is to provide novel reaction monomers intended for the preparation of polyurethanes without the presence of isocyanates.

The present invention concerns compounds of the following formula (I):

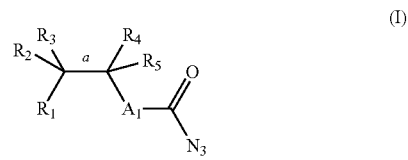

in which:

$R_1$ is a straight-chain or branched alkyl group comprising 1 to 20 carbon atoms, optionally substituted by one or more $OR_a$ substituents, $R_a$ representing a hydrogen atom or an alkyl group comprising 1 to 20 carbon atoms, the said group $R_1$ optionally containing one or more unsaturations;

a is a single or double bond;

$R_2$ is a hydrogen atom, an $OR_a$ group, $R_a$ representing a hydrogen atom or an alkyl group comprising 1 to 20 carbon atoms, or a straight-chain or branched alkyl group comprising 1 to 20 carbon atoms substituted by an OH group, or $R_2$ represents a radical of formula —$(OCH_2CH_2)_n$—OH or —$CH_2$—$(CH_2OCH_2)_n$—$CH_3$, n representing an integer of between 1 to 100, preferably 6 to 50, preferably it is 6, 13 or 45;

$R_3$, when a is a single bond, represents a hydrogen atom or, when a is a double bond, $R_3$ is absent;

$R_4$ is a hydrogen atom or an $OR_b$ group, $R_b$ representing a hydrogen atom or an alkyl group comprising 1 to 20 carbon atoms, or a straight-chain or branched alkyl group comprising 1 to 20 carbon atoms, substituted by an OH group, or $R_4$ is a radical of formula —$(OCH_2CH_2)_n$—OH or —$CH_2$—$(CH_2OCH_2)_n$—$CH_3$, n representing an integer of between 1 and 100, preferably between 6 and 50, and preferably it is 6, 13 or 45;

$R_5$, when a is a single bond, represents a hydrogen atom, or when a is a double bond $R_5$ is absent; and $A_1$ is a divalent, straight-chain or branched, alkylene radical comprising 1 to 20 carbon atoms, the said alkylene radical optionally containing one or more unsaturations.

In the present invention, when the radical $A_1$ comprises one or more unsaturations, it is possible to envisage a subsequent functionalization step of the above-mentioned formula (I) compound. This step allows chemical modifications to be added onto the unsaturation(s). For example an epoxidation step can be contemplated followed by ring opening, which allows the inserting of hydroxyl groups into the $A_1$ chain. Similarly, if $R_1$ comprises one or more unsaturations, it is possible to envisage a subsequent functionalization step of the above-mentioned formula (I) compound. This step allows chemical modifications to be added onto the unsaturation(s). For example an epoxidation step can be envisaged followed by ring opening, which allows the inserting of hydroxyl groups into the $R_1$ chain.

According to the present invention, the "alkyl" radicals represent saturated hydrocarbon radicals, straight-chain or branched, comprising 1 to 20 carbon atoms, in particular 1 to 12 carbon atoms, preferably 1 to 10 carbon atoms, and further preferably 1 to 5 carbon atoms (they may typically be represented by the formula $C_nH_{2n+1}$, n representing the number of carbon atoms). When they are straight-chain particular mention may be made of methyl, ethyl, propyl, butyl, pentyl, hexyl, octyl, nonyl and decyl radicals. When they are branched or substituted by one or more alkyl radicals, particular mention may be made of the isopropyl, tert-butyl, 2-ethylhexyl, 2-methylbutyl, 2-methylpentyl, 1-methylpentyl and 3-methylheptyl radicals. The term "alkyl" also designates the cycloalkyl radicals which are mono-, bi- or tricyclic hydrocarbon radicals, saturated or partly unsaturated, non-aromatic, comprising 3 to 20 carbon atoms, and preferably 3 to 10 carbon atoms such as cyclopropyl, cyclopentyl, cyclohexyl or adamantly in particular, and the corresponding rings containing one or more unsaturations.

The above-mentioned "alkyl" radicals may be substituted by one or more substituents. Among these substituents, mention may be made of the following groups: amino, hydroxy, thio, halogen, carboxyl, alkyl, alkoxy, alkylthio, alkylcarbonyl, alkylcarboxyl, alkylamino, aryloxy, arylalkoxy, cyano, trifluoromethyl, alkylsulfonyl, carboxy or carboxyalkyl.

The "alkoxy" radicals according to the present invention are radicals of the formula —O-alkyl, the alkyl group being such as defined in the foregoing.

The term "alkylthio" designates an —S-alkyl group, the alkyl group being such as defined above.

The term "alkylamino" designates a —NH-alkyl group, the alkyl group being such as defined above.

The term "alkylcarbonyl" designates a —CO-alkyl group, the alkyl group being such as defined above.

The term "alkylcarboxyl" designates a —COO-alkyl group, the alkyl group being such as defined above.

The term "alkylsulfonyl" designates a —SO$_2$-alkyl group, the alkyl group being such as defined above.

Among the halogen atoms, particular mention is made of the fluorine, chlorine, bromine and iodine atoms.

The term "aryloxy" designates an —O-aryl group, the aryl group being such as defined above.

The term "arylalkoxy" designates an aryl-alkoxy- group, the aryl and alkoxy groups being such as defined above.

The term "carboxyalkyl" designates a HOOC-alkyl- group, the alkyl group being such as defined above. As examples of carboxyalkyl groups, particular mention may be made of carboxymethyl or carboxyethyl.

When an alkyl radical is substituted by an aryl group, the term "arylalkyl" or "aralkyl" radical is used. The <<arylalkyl>> or <<aralkyl>> radicals are aryl-alkyl- radicals, the aryl and alkyl groups being such as defined above. Among the arylalkyl radicals, particular mention may be made of the benzyl or phenethyl radical. These arylalkyl groups can be substituted by one or more substituents. Amongst these substituents, mention may be made of the following groups: amino, hydroxy, thio, halogen, carboxyl, alkyl, alkoxy, alkylthio, alkylcarbonyl, alkylcarboxyl, alkylamino, aryloxy, arylalkoxy, cyano, trifluoromethyl, alkylsulfonyl, carboxy or carboxyalkyl.

According to the present invention, the "alkylene" radicals represent radicals (also called alkylidenes) derived from alkanes whose two terminal hydrogen atoms have been removed. When the said alkylene radicals are straight-chain they may represented by the formula —$(CH_2)_n$—.

Preferably, in the above-mentioned formula (I), R1 is an alkyl group, in particular comprising 8 carbon atoms.

In the above-mentioned formula (I), $R_1$ may also advantageously represent an alkyl group substituted by an OH group, and more particularly a $CH_3(CH_2)_5CH(OH)CH_2$ group.

Preferably, in the above-mentioned formula (I), R2 is an OH group.

In the above-mentioned formula (I), $R_2$ may also advantageously represent H.

Preferably, in the above-mentioned formula (I), $R_4$ is an alkoxy $OR_b$ group, $R_b$ representing an alkyl group, and more particularly $R_4$ may be an OMe group.

In the above-mentioned formula (I), $R_4$ may also advantageously represent H.

According to one advantageous embodiment, the present invention concerns compounds of formula (I) such as defined above, in which at least one of the groups $R_1$, $R_2$ and $R_4$ comprises an OH or alkoxy group.

According to another advantageous embodiment, the present invention concerns compounds of formula (I) such as defined above in which, when a represents a single bond, at least one of the groups $R_2$ and $R_4$ comprises an OH or alkoxy group.

The present invention also concerns the preferred compounds of the following formula (I-1):

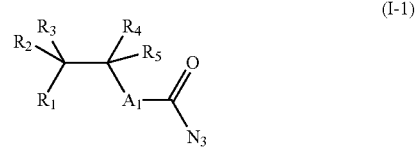
(I-1)

in which:
$R_1$ is a straight-chain or branched alkyl group, comprising 1 to 20 carbon atoms, optionally substituted by one or more $OR_a$ substituents, $R_a$ representing a hydrogen atom or an alkyl group comprising 1 to 20 carbon atoms, the said $R_1$ group optionally containing one or more unsaturations;

$R_2$ is a hydrogen atom, an $OR_a$ group, $R_a$ representing a hydrogen atom or an alkyl group comprising 1 to 20 carbon atoms, or a straight-chain or branched alkyl group comprising 1 to 20 carbon atoms, substituted by an OH group, or $R_2$ is a radical of formula —$(OCH_2CH_2)_n$—OH or —$CH_2$—$(CH_2OCH_2)_n$—$CH_3$, n representing an integer of 1 to 100, preferably 6 to 50, and is preferably 6, 13 or 45;

$R_3$ is a hydrogen atom;

$R_4$ is a hydrogen atom or an $OR_b$ group, $R_b$ representing a hydrogen atom or an alkyl group comprising 1 to 20 carbon atoms, or a straight-chain or branched alkyl group comprising 1 to 20 carbon atoms, substituted by an OH group, or $R_4$ is a radical of formula —$(OCH_2CH_2)_n$—OH or —$CH_2$—$(CH_2OCH_2)_n$—$CH_3$, n representing an integer of 1 to 100, preferably 6 to 50 and is preferably 6, 13 or 45;

$R_5$ is a hydrogen atom; and $A_1$ is a divalent alkylene radical, straight-chain or branched, comprising 1 to 20 carbon atoms, the said alkylene radical optionally containing one or more unsaturations.

The formula (I-1) compounds correspond to formula (I) compounds such as defined above in which a represents a single bond.

According to one advantageous embodiment, the present invention concerns compounds of formula (I-1) such as defined above in which at least one of the groups $R_2$ and $R_4$ comprises an OH or alkoxy group.

The present invention also concerns the preferred compounds of the following formula (I-2):

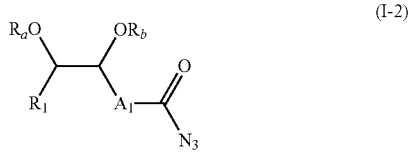
(I-2)

in which:

$R_1$ is a straight-chain or branched alkyl group comprising 6 to 12 carbon atoms;

$R_a$ is a hydrogen atom or an alkyl group comprising 1 to 12 carbon atoms;

$R_b$ is a hydrogen atom or an alkyl group comprising 1 to 12 carbon atoms; and $A_1$ is a divalent alkylene radical, straight-chain or branched, comprising 6 to 12 carbon atoms.

The compounds of formula (I-2) correspond to compounds of formula (I) such as defined above, in which a represents a single bond, $R_3$ is H, $R_2$ is an $OR_a$ group, $R_4$ is an ORb group and $R_5$ is H.

According to one particular embodiment, the present invention concerns the compounds of formula (I-2) such as defined above in which $R_a$ is H.

According to one particular embodiment, the present invention concerns the compounds of formula (I-2) such as defined above in which $R_b$ is a methyl group.

According to one particular embodiment, the present invention concerns the compounds of formula (I-2) such as defined above, in which $A_1$ is an alkylene radical, in particular straight-chain, comprising 7 carbon atoms.

According to one particular embodiment, the present invention concerns the compounds of formula (I-2) such as defined above in which $R_1$ is an alkyl group, in particular straight-chain, comprising 8 carbon atoms.

Therefore, the present invention also concerns the preferred compound of the following formula (I-3):

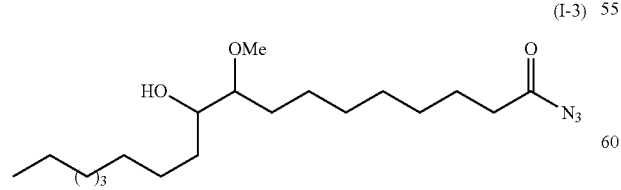
(I-3)

This compound is called HMODAz in the remainder hereof. It is the azide of 10-hydroxy-9-methoxyoctadecanoyl which is a novel monomer of type AB obtained from sunflower oil.

The present invention also concerns the compounds of the following formula (I-4):

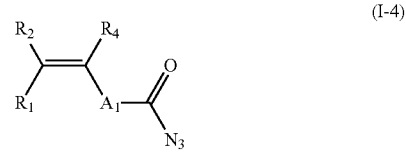
(I-4)

in which:

$R_1$ is a straight-chain or branched alkyl group comprising 1 to 20 carbon atoms, optionally substituted by one or more $OR_a$ substituents, $R_a$ representing a hydrogen atom or an alkyl group comprising 1 to 20 carbon atoms, the said group $R_1$ optionally containing one or more unsaturations;

$R_2$ is a hydrogen atom, an $OR_a$ group $R_a$ representing a hydrogen atoms or an alkyl group comprising 1 to 20 carbon atoms, or a straight-chain or branched alkyl group comprising 1 to 20 carbon atoms substituted by an OH group, or $R_2$ is a radical of formula $-(OCH_2CH_2)_n-OH$ or $-CH_2-(CH_2OCH_2)_n-CH_3$, n representing an integer of between 1 to 100, preferably 6 to 50, and is preferably 6, 13 or 45;

$R_4$ is a hydrogen atom or an $OR_b$ group, $R_b$ representing a hydrogen atom or an alkyl group comprising 1 to 20 carbon atoms, or a straight-chain or branched alkyl group comprising 1 to 20 carbon atoms substituted by an OH group, or $R_4$ is a radical of formula $-(OCH_2CH_2)_n-OH$ or $-CH_2-(CH_2OCH_2)_n-CH_3$, n representing an integer of 1 to 1000, preferably 6 to 50, and is preferably 6, 13 or 45;

$A_1$ is a divalent alkylene radical, straight-chain or branched, comprising 1 to 20 carbon atoms, the said alkylene radical optionally containing one or more unsaturations.

The formula (I-4) compounds correspond to compounds of formula (I) such as defined above in which a represents a double bond and $R_3$ and $R_5$ are absent.

Preferably in the above-mentioned formula (I-4), $R_2$ is H.

Preferably in the above-mentioned formula (I-4), $R_4$ is H.

Therefore, among the compounds of formula (I-4) such as defined above, the compounds of the following formula (I-5) can be cited:

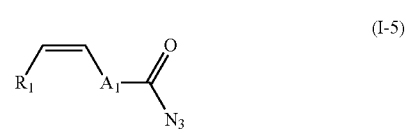
(I-5)

in which:

$R_1$ is a straight-chain or branched alkyl group comprising 6 to 12 carbon atoms, optionally substituted by an OH group, $A_1$ is a divalent alkylene radical, straight-chain or branched, comprising 6 to 12 carbon atoms.

The formula (I-5) compounds correspond to compounds of formula (I) such as defined above in which a represents a double bond, $R_3$ and $R_5$ are absents and $R_2$ and $R_4$ are H.

Preferably, in the above-mentioned formula (I-5), $R_1$ is an alkyl group substituted by an OH group.

Therefore, the present invention also concerns compounds of the following formula (I-6):

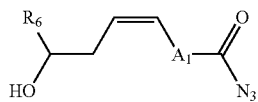
(I-6)

in which:

$A_1$ is such as defined for formula (I-5), and $R_6$ is an alkyl group, straight-chain or branched, comprising 1 to 12 carbon atoms.

Among the preferred compounds of the invention, mention can be made of the following formula (I-7):

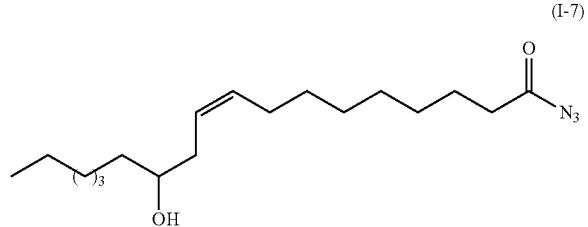
(I-7)

This compound is called HODEAz in the remainder hereof. It is the azide of 12-hydroxy-octadec-9-ecanoyl which is a novel monomer of AB type obtained from castor oil.

The present invention also concerns a method for preparing a compound of formula (I) such as defined above comprising a step to react a compound of the following formula (II):

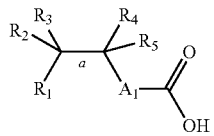
(II)

in which $R_1$, $R_2$, $R_3$, $R_4$, $R_5$, $A_1$ and a, are such as defined above for formula (I), with ethyl chloroformate in the presence of triethylamine, then with sodium azide.

Preferably, the reaction step of the above-mentioned formula (II) compound is conducted in two stages: the first comprises reacting compound (II) with the ethyl chloroformate in the presence of triethylamine in a THF/water mixture for 2 hours at 0° C., and the second stage then comprises causing the intermediate compound obtained after the first stage to react with sodium azide in water for 4 hours at 0° C.

The present invention also concerns the use of a compound of formula (I) such as defined above, for the preparation of polyurethane.

More particularly, the present invention concerns the use of a compound of formula (I-2) or (I-3), for the preparation of polyurethane meeting the following formula (III-1):

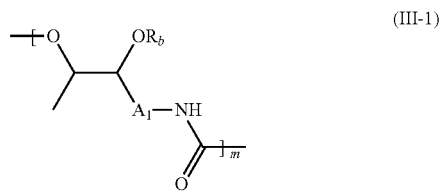
(III-1)

$A_1$, $R_1$ and $R_b$ being such as defined above for formula (I-2), and m representing an integer of 2 to 50 000, preferably 2 to 10 000, more preferably 2 to 5 000 and further preferably 2 to 50.

More particularly, the present invention concerns the use of a compound of formula (I-3) such as defined above, for the preparation of polyurethane meeting the following formula (III-1-1):

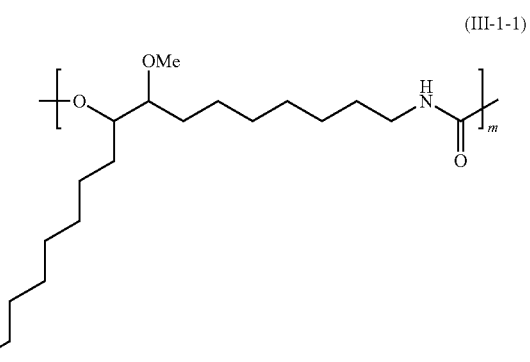
(III-1-1)

m representing an integer of 2 to 50 000, preferably 2 to 10 000, more preferably 2 to 5 000 and further preferably 2 to 50.

The present invention also concerns the use of a formula (I) compound, and more particularly a compound of formula (I-4), (I-5), (I-6) or (I-7), for the preparation of polyurethane meeting the following formula (III-2):

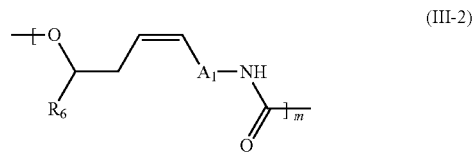
(III-2)

$R_6$ and $A_1$ being such as defined above for formula (I-6), and m representing an integer of 2 to 50 000, preferably 2 to 10 000, more preferably 2 to 5 000 and further preferably 2 to 50.

More particularly, the present invention concerns the use of a formula (I-7) compound such as defined above, for the preparation of polyurethane meeting the following formula (III-2-1):

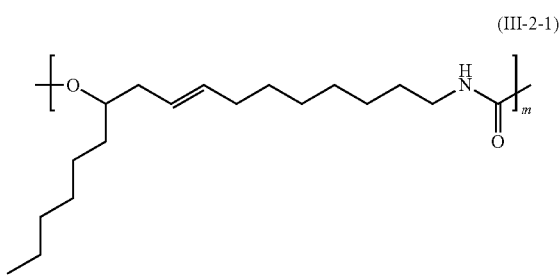

(III-2-1)

m representing an integer of 2 to 50 000, preferably 2 to 10 000, more preferably 2 to 5 000, and further preferably 2 to 50.

The present invention also concerns the use of a compound of formula (I) and more particularly a compound of formula (I-4), (I-5), (I-6) or (I-7), for preparing polyurethane meeting the following formula (III-3):

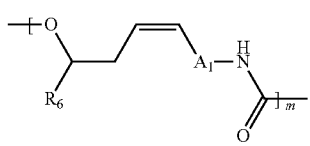

(III-3)

m representing an integer of 2 to 50 000, preferably 2 to 10 000, more preferably 2 to 5 000 and further preferably 2 to 50.

$R_6$ and $A_1$ being such as defined above for formula (I-6).

More particularly, the present invention concerns the use of a compound of formula (I-7) such as defined above for the preparation of polyurethane meeting the following formula (III-3-1):

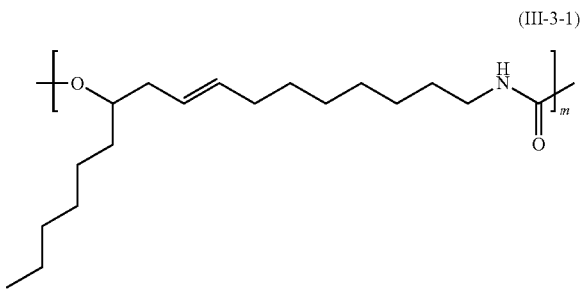

(III-3-1)

m representing an integer of 2 to 50 000, preferably 2 to 10 000, more preferably 2 to 5 000 and further preferably 2 to 50.

The present invention also concerns a method for preparing polyurethane, particularly meeting any one of formulas (III-1), (III-1-1), (III-2) or (111-2-1), comprising a self-condensing step of a compound of formula (I) such as defined above at a temperature of between 50° C. and 100° C., preferably 80° C., for a time of 1 hour to 48 hours, preferably for 24 hours.

The present invention also concerns a method for preparing polyurethane, in particular meeting any one of formulas (III-3) or (III-3-1), comprising the following steps:

a reaction step of a formula (I) compound such as defined above with an alcohol $R_7OH$, $R_7$ representing a straight-chain or branched alkyl group comprising 1 to 4 carbon atoms, $R_7$ preferably being a methyl group to obtain a compound of the following formula (IV):

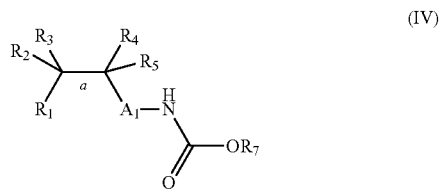

(IV)

in which $R_1$, $R_2$, $R_3$, $R_4$, $R_5$, $A_1$ and a, are such as defined above in formula (I), and a polycondensation step of the formula (IV) compound in the presence of titanium tetrabutoxide at a temperature of between 80° C. to 180° C., preferably at 130° C., for a time of 2 hours to 48 hours, preferably for 6 hours.

Preferably the first step of this method is conducted under reflux for 4 hours.

EXAMPLES

Example 1

Synthesis of HMODAz—Compound of Formula (I-3)

Figure 1:
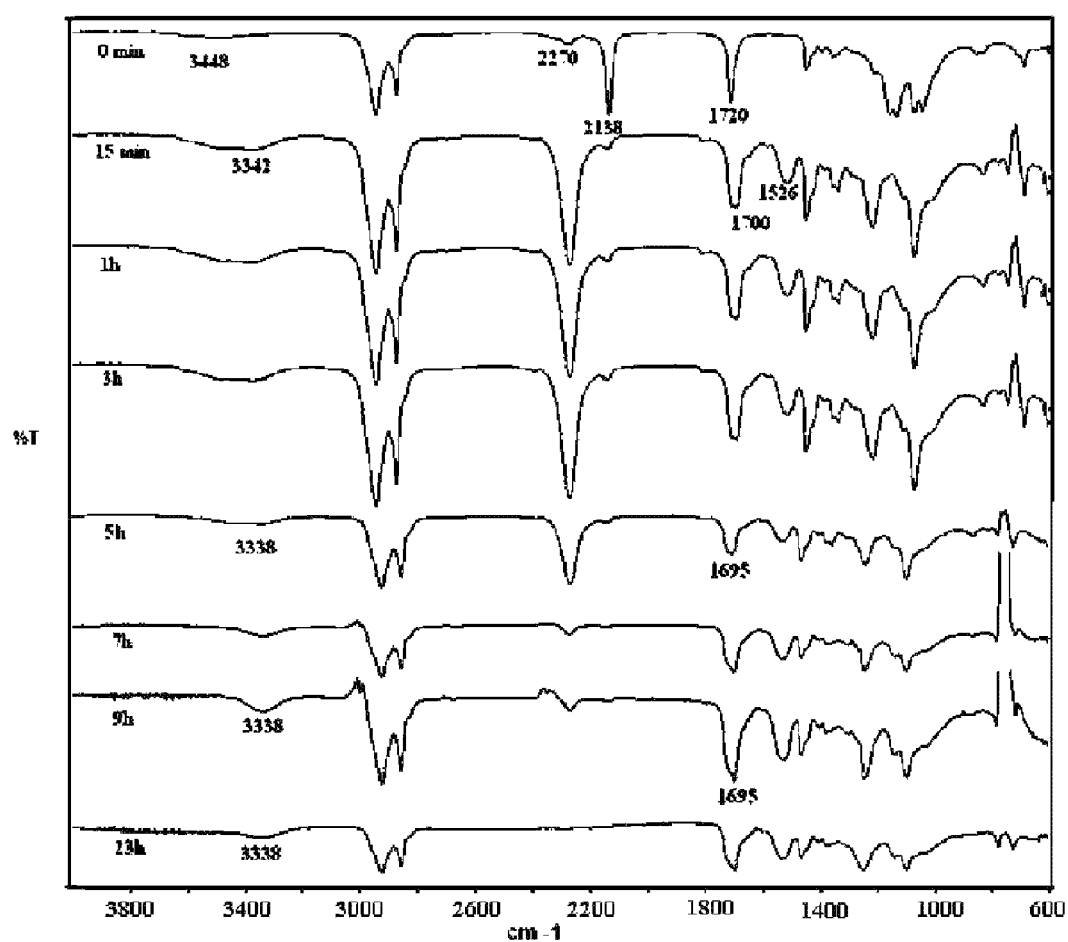
FIG. 1 shows a FTIR spectrum (Fourier Transform Infrared Spectroscopy) of samples of polymerisation of HMODAz (5) after different polymerisation times.

The HMODAz compound (compound 5 below) was prepared following the reaction scheme described below:

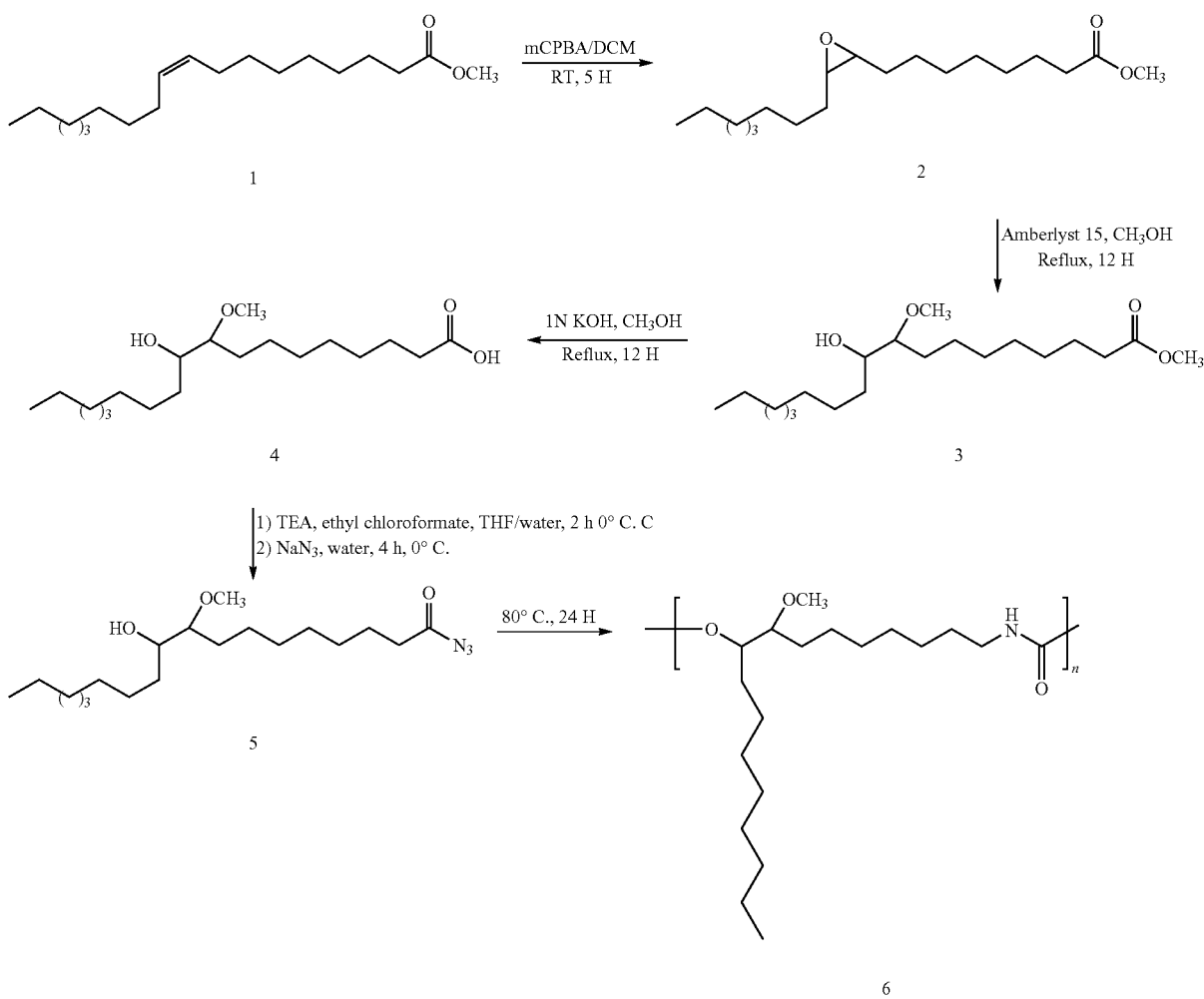

The monomer (5) was obtained from a natural source: sunflower oil transesterfied with methanol in the presence of MgO as catalyst.

This monomer HMODAz was synthesized using a method having five main steps.

Synthesis of methyl 8-(3-octyloxiran-2-yl)octanoate (2)

Methyl oleate (1) (5.0 g; 0.017 mol) (89%) (ITERG) and meta-chloroperbenzoic acid (mCPBA) (4.3 g; 0.025 mol) (Aldrich) were dissolved in dichloromethane (J. T. Baker) (100 mL) and the reaction mixture was mixed under agitation at ambient temperature for 5 hours. The reaction mixture was then filtered and the collected solution was washed with saturated aqueous sodium bicarbonate (3×50 mL) (Aldrich) then with water (3×50 mL). The organic layer was separated and dried over anhydrous sodium sulfate. Finally, the solvent was removed by evaporation under rotation to obtain the intermediate compound 2.

Yield: 4.8 g (91%)
IR: 1740 cm$^{-1}$ (COOCH$_3$), 841 cm$^{-1}$ (epoxy).
$^1$H-NMR (400 MHz, CDCl$_3$): 0.87 (3H, t, CH$_3$); 1.20-1.70 (methylene protons); 2.29 (2H, t, CH$_2$—COOCH$_3$); 2.99 (2H, epoxy cycle protons); 3.66 (3H, s, COOCH$_3$).

Synthesis of methyl 10-hydroxy-9-methoxyoctadecanoate (3)

The methyl 8-(3-octyloxiran-2-yl)octanoate (2) (4.8 g; 0.015 mol), Amberlyst 15 (0.05 g) and methanol in excess (100 mL) were placed under reflux for 12 hours. The reaction mixture was filtered and the methanol removed using a rotary evaporator. The reaction mixture was dissolved in dichloromethane (100 mL) and washed with water (3×50 mL). The dichloromethane solution was separated and evaporated to obtain the intermediate compound 3.

Yield: 4.7 g (89%)
IR: 3476 cm$^{-1}$ (OH), 1740 cm$^{-1}$ (COOCH$_3$),
$^1$H-NMR (400 MHz, CDCl$_3$): 0.88 (3H, t, CH$_3$); 1.20-1.70 (methylene protons); 2.29 (2H, t, CH$_2$—COOH); 2.99 (1H, q, CH—OCH$_3$); 3.41 (3H, s, OCH$_3$); 3.49 (1H, m, CH—OH); 3.66 (3H, s, COOCH$_3$).

Synthesis of 10-hydroxy-9-methoxyoctadecanoic acid (4)

The methyl 10-hydroxy-9-methoxyoctadecanoate (3) (4.0 g; 0.012 mol) was dissolved in 1N methanol sodium hydroxide solution (100 mL) (Aldrich) and heated under reflux for 12 h. The methanol was removed from the reaction mixture and the crude product was dissolved in 100 mL water. The aqueous solution was neutralised with hydrochloric acid (Aldrich) and the product extracted with 3×50 mL dichloromethane (J. T. Baker). The dichloromethane solution was washed with 3×50 mL water and dried over anhydrous sodium sulfate (J. T. Baker). The dichloromethane solution was filtered and the solvent was removed to obtain the intermediate compound 4.

Yield: 3.50 g (91%)

IR: 3435 cm$^{-1}$ (OH), 1709 cm$^{-1}$ (COOH).

$^1$H-NMR (400 MHz, CDCl$_3$): 0.86 (3H, t, CH$_3$); 1.20-1.70 (methylene protons); 2.34 (2H, t, CH$_2$—COOH); 2.98 (1H, q, CH—OCH$_3$); 3.39 (3H, s, OCH$_3$); 3.47 (1H, m, CH—OH).

$^{13}$C-NMR (400 MHz, CDCl$_3$): 179.32 ppm (COOH); 84.41 ppm (CH—OMe); 72.20 ppm (CH—OH); 58.31 ppm (OCH$_3$); 22-35 ppm (alkyl chain protons) and 13.90 ppm (CH$_3$).

Synthesis of the type AB monomer: azide of 10-hydroxy-9-methoxyoctadecanoyl (HMODAz) (5)

To a 100 mL round-bottomed flask equipped with a magnetic stirrer and an addition funnel were added the 10-hydroxy-9-methoxyoctadecanoic acid (4) (2.0 g; 0.006 mol), triethylamine (Aldrich) (1.8 g; 0.018 mol) and the THF/water mixture (7:3 v/v, 30 mL). The reaction mixture was cooled to 0° C. and chloroethyl formate (Fluka) (1.96 g; 0.018 mol) was added drop-wise over 10 minutes. The reaction mixture was agitated for 2 hours then sodium azide (Aldrich) (1.2 g; 0.018 mol) in water (7 mL) was added drop-wise over 10 minutes and stirred at 0° C. for 4 hours. The THF was removed in a rotary evaporator and the crude product collected was dissolved in dichloromethane (100 mL). The dichloromethane solution was washed with water (2×50 mL), dried over anhydrous sodium sulfate (J. T. Baker), filtered and the solvent was removed to obtain the compound HMODAz (5).

Yield: 2.0 g (92%)

IR: 3465 cm$^{-1}$ (OH), 2138 cm$^{-1}$ (N$_3$), 1720 cm$^{-1}$ (CO).

$^1$H-NMR (400 MHz, CDCl$_3$): 0.87 (3H, t, CH$_3$); 1.20-1.70 (methylene protons); 2.32 (2H, t, CH$_2$—CON$_3$); 2.98 (1H, q, CH—OCH$_3$); 3.39 (3H, s, OCH$_3$); 3.47 (1H, m, CH—OH).

$^{13}$C-NMR (400 MHz, CDCl$_3$): 180.09 (CON$_3$); 84.11 (CH—OMe); 72.23 (CH—OH); 57.73 (OCH$_3$); 21-37 (alkyl chain protons) and 13.54 (CH$_3$).

The HMODAz monomer (5) is a self-condensable monomer with a secondary hydroxyl group and an acyl azide group as precursor of the isocyanate function.

Polymerisation by AB-Type Self-Condensation of HMODAz (5)

To a twin-neck, round-bottomed flask of 50 ml equipped with a magnetic stirrer and a nitrogen inlet, was added the azide of 10-hydroxy-9-methoxyoctadecanoyl (5) (2.0 g; 0.005 mol) and the assembly was held in an oil bath at different temperatures (50° C., 60° C., 80° C. and 110° C.) for different times.

Yield: 1.80 g (90%)

IR: 3 338 cm$^{-1}$ (NH), 1695 cm$^{-1}$ (CO), 1 526 cm$^{-1}$ (NH deformation), 1 230 cm$^{-1}$ (C—N).

$^1$H-NMR (400 MHz, CDCl$_3$): 0.87 (CH$_3$); 1.20-1.70 (methylene protons); 3.18 (—CH$_2$—NHCOO); 3.39 (OCH$_3$); 4.88 (NH).

Example 2

Synthesis HODEAz—Compound of Formula (I-7)

The HODEAz compound (compound 8 hereunder) was prepared following the reaction scheme described below:

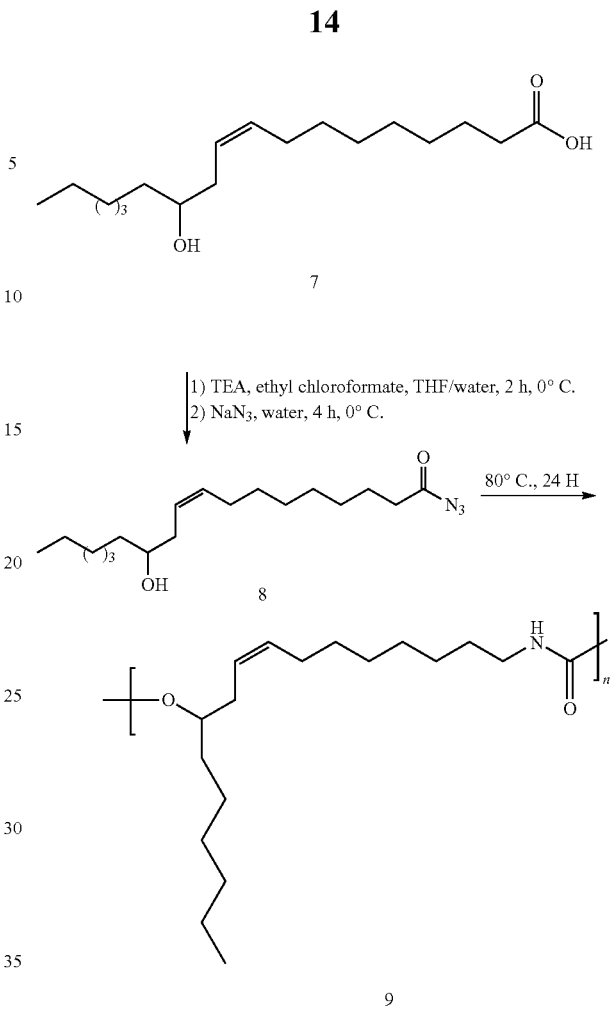

Synthesis of AB-type monomer: azide of 12-hydroxy-octadec-9-enoyl (HODEAz) (8)

Similar procedure to the procedure followed for the synthesis of HMODAz (5) (cf. Example 1) was applied to the synthesis of the HODEAz monomer (8) of AB-type starting from ricinoleic acid (80%) (TCI Chemicals).

Ricinoleic acid is a C18 fatty acid comprising an OH group with C9 double bond in cis configuration.

Yield: 90%

IR: 3400 cm$^{-1}$ (OH), 3008 (=C—H), 2133 cm$^{-1}$ (N$_3$), 1720 cm$^{-1}$ (CO).

$^1$H-NMR (400 MHz, CDCl$_3$): 0.87 (3H, t, CH$_3$); 1.20-1.70 (methylene protons); 2.31 (2H, t, CH$_2$—CON$_3$); 3.58 (1H, m, CH—OH); 5.3-5.6 (CH=CH).

$^{13}$C-NMR (400 MHz, CDCl$_3$): 180.53 (CON$_S$); 132.96 and 125.31 (CH=CH); 71.38 (CH—OH); 42.88 (CH$_2$CON$_3$); 36.78 and 35.25 (CH$_2$—CH(OH)—CH$_2$); 21-37 (alkyl chain protons) and 13.54 (CH$_3$).

Polymerisation by AB-Type Self-Condensation of HODEAz (8)

For polymerisation leading to the polymers of formula (9), the procedure followed is the one indicated above under Example 1 for the polymer of formula (6).

Example 3

Self-Condensation of HMODAz, Characterisation and Monitoring of the Progress of the Reaction The synthesis of polyurethanes according to the present invention is based on the self-condensation of sodium azide and of the hydroxyl groups. This technique has the following advantages: i) the reaction takes place under gentle conditions through mere heating of the monomer using a 'one pot' method; and ii) no optimisation of molar ratios is needed.

The self-condensation of the HMODAz monomer (5) was produced at different temperatures such as 50° C., 60° C., 80° C. and 110° C. Table 1 below indicates the detailed conditions of the reaction and the results of polymerisation.

TABLE 1

Experimental conditions and results for the polymerisation of HMODAz (compound 5)

| Test | Temperature (° C.) | Time (h) | $M_n$ | SEC[b] $M_w$ | $M_w/M_n$ |
|---|---|---|---|---|---|
| 1 | 50 | 20 | 3210 | 4880 | 1.52 |
| 2[c] | 50 | 5 | 2720 | 4280 | 1.57 |
| 3 (i) | 60 | 8 | 1040 | 1620 | 1.55 |
| 3 (ii) | 60 | 23 | 2475 | 3780 | 1.52 |
| 4 (i) | 80 | 1 | 740 | 1740 | 2.33 |
| 4 (ii) | 80 | 2 | 1640 | 3240 | 1.97 |
| 4 (iii) | 80 | 3 | 2510 | 4820 | 1.92 |
| 4 (iv) | 80 | 5 | 2610 | 3880 | 1.48 |
| 4 (v) | 80 | 7 | 3510 | 6030 | 1.71 |
| 4 (vi) | 80 | 9 | 3660 | 6340 | 1.73 |
| 4 (vii) | 80 | 23 | 6390 | 10450 | 1.63 |
| 5[c] | 80 | 6 | 8890 | 18740 | 2.10 |
| 6 | 110 | 4 | 3500 | 6310 | 1.80 |

[b]based on PS calibration;
[c]reaction in the presence of DBTDL (0.1 wt. % relative to HMODAz) as catalyst.

It was found that all the temperatures used for the polymerisations are efficient. Temperature has a crucial effect on the decomposition of acyl azide and the rate of polymerisation. For example, by comparing test n° 1 (conducted at 50° C.) with test 4(vii) (conducted 80° C.), it is ascertained that higher molecular weights are obtained when operating at 80° C.

For a more complete analysis of the progress of the reaction, different polymerisation tests were conducted at 80° C.

Figure 2:
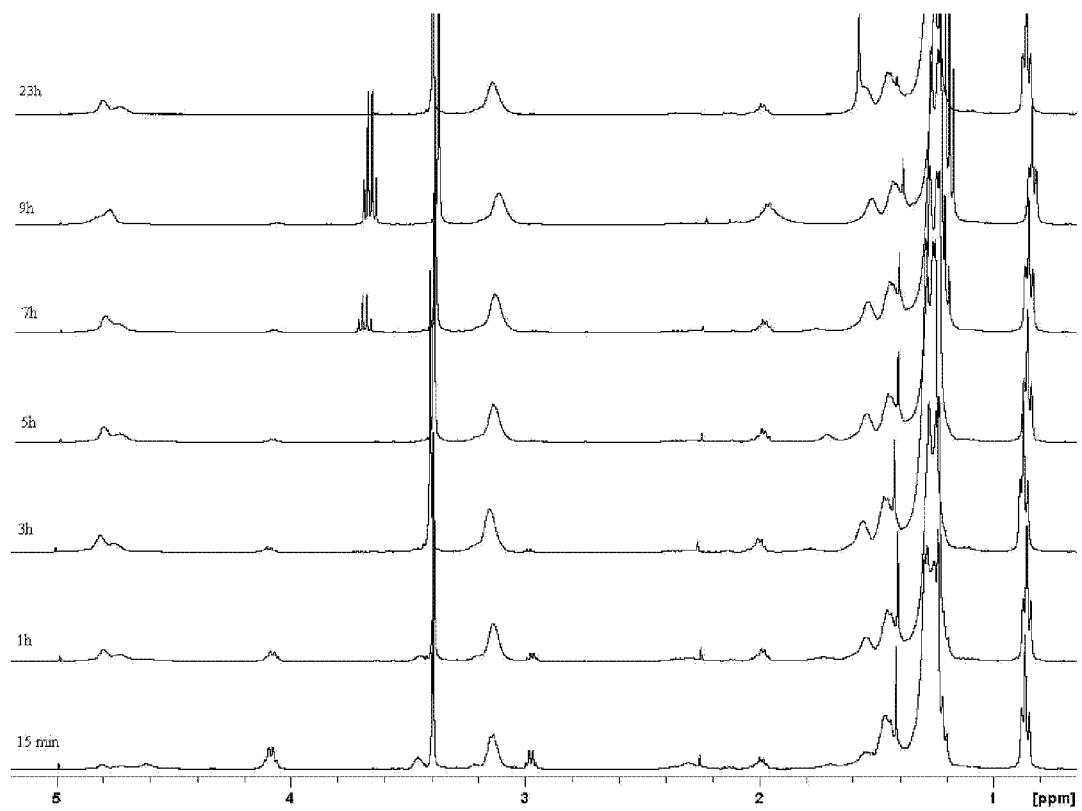
FIG. 2 gives the NMR spectrum of the ($^1$H-NMR) proton of samples of polymerisation of HMODAz (5) at different time intervals.
Figure 3:
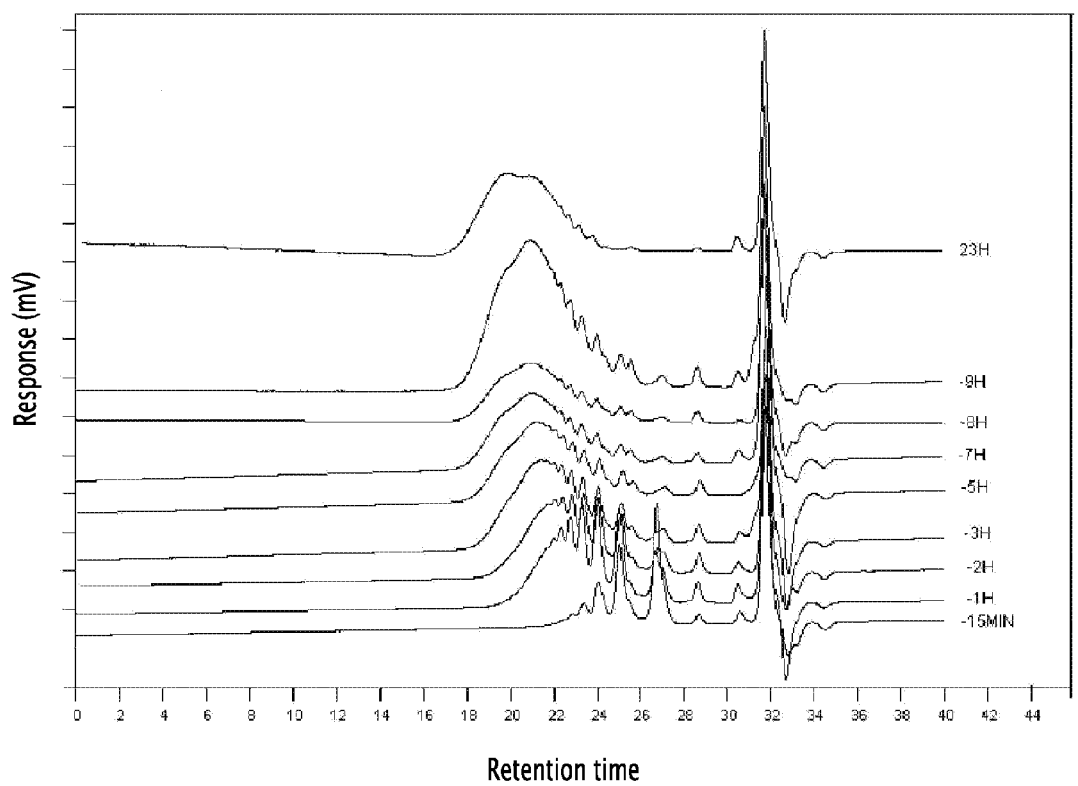
FIG. 3 illustrates the analyses performed using size exclusion chromatography (SEC) of samples of polymerisation of HMODAz (compound 5) as a function of time.

FIGS. 1 and 2 respectively illustrate the FTIR and $^1$H-NMR spectra of the progress of polymerisation, and FIG. 3 illustrates the SEC spectrum monitoring the reaction.

The band at 2 138 cm$^{-1}$ due to the presence of the acyl azide group (CON$_3$) is replaced by a band at 2 270 cm$^{-1}$ corresponding to the isocyanate functions when heating to 80° C. The absorption band at 3 341 cm$^{-1}$ is observed on account of the N—H urethane bond. The samples taken after 15 minutes during the progress of the reaction show near-complete transformation of the acyl-azide group to an isocyanate group according to the IR spectrum (FIG. 2). After FTIR analysis, the samples were left to react with ethanol and analysed by $^1$H-NMR spectroscopy. A peak was observed at 4.06 ppm (Hg) on account of the presence of the protons of the methylene group bonded to the urethane group (FIG. 2).

The FTIR spectra of the samples show that when the polymerisation time is increased, the intensity of the isocyanate band (2 270 cm$^{-1}$) decreases accordingly, whilst the intensity of the N—H band (3 338 cm$^{-1}$) increases due to the formation of polyurethane. The band of the carbonyl group of acyl azide at 1 720 cm$^{-1}$ moves at lower frequencies (1 695 cm$^{-1}$) due to the formation of the urethane bond.

Similar conclusions were obtained with the $^1$H-NMR spectra. The intensity of the peak at 4.06 ppm concerning the methylene protons attached to the carbamate group (NH—COO—CH$_2$CH$_3$) as terminal group decreases over time (15 min, 1 h, 3 h, etc.) due to the increase in molecular weight of the polyurethane (FIG. 2). An increase in the intensities of the peaks at 4.80 ppm was also observed due to the NH protons of the urethane groups and a peak at 3.16 ppm due to the protons of the methylene radical bonded to the urethane group of the polyurethane (—CH$_2$—NH—COO—).

The results of SEC chromatography show that a sample obtained after 15 min shows the formation of traces of di-, tri- and tetramer and a larger fraction of isocyanate monomer (FIG. 3). When the polymerisation time is increased, the intensities of the SEC peaks corresponding to the oligomers decrease and the SEC peaks move towards higher molecular weights, illustrating the mechanism of polycondensation.

Example 4

Self-Condensation of HODEAz, Characterisation and Monitoring of the Progress of the Reaction The self-condensation of the HODEAz monomer (8) was produced at different temperatures such as 60° C. and 80° C. Table 2 below indicates the detailed conditions of the reaction and the results of polymerisation.

TABLE 2

Experimental conditions and results for the polymerisation of HODEAz (compound 8)

| Test | Temperature (° C.) | Time (h) | $M_n$ | SEC[b] $M_w$ | $M_w/M_n$ |
|---|---|---|---|---|---|
| 7 | 60 | 24 | 5300 | 7770 | 1.47 |
| 8 | 80 | 10 | 6210 | 9330 | 1.50 |
| 9 | 80 | 24 | 6880 | 10030 | 1.46 |

[b]based on PS calibration

It is ascertained in this table that the molecular weight of the polyurethane synthesised at 60° C. is lower than that of the polyurethane obtained by self-condensation at 80° C.

Example 5

Analysis by Differential Scanning Calorimetry

Figure 4:
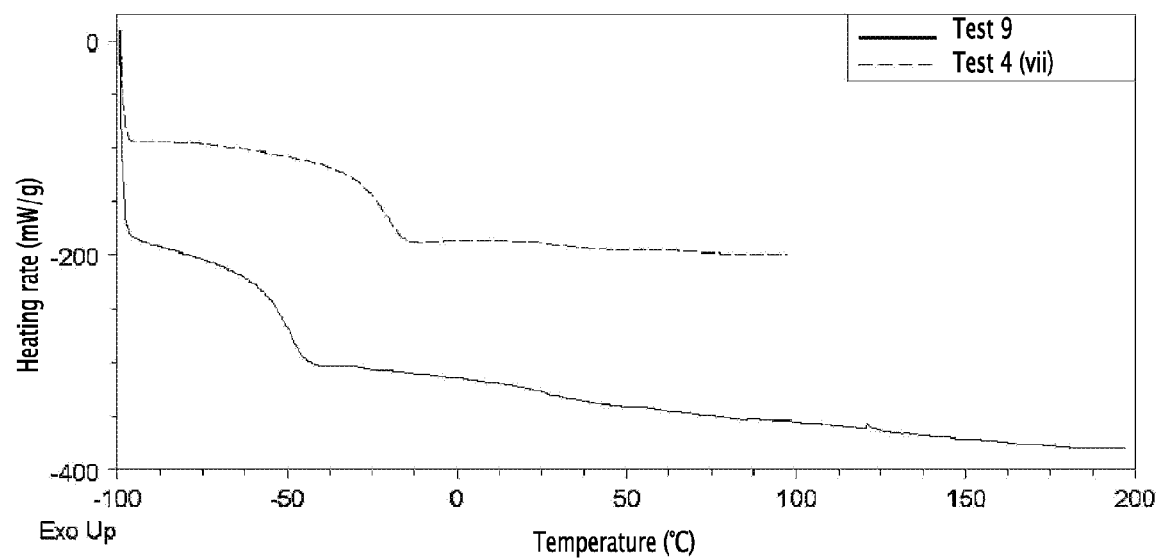
FIG. 4 gives DSC thermograms (Differential Scanning Calorimetry) of the polyurethanes (6) [compound of formula (III-1-1)] and (9) (compound of formula (III-2-1)].

FIG. 4 illustrates DSC thermograms for the polyurethanes derived from HMODAz (5) and HODEAz (8) by self-condensation at a heating rate of 10° C./min. The glass transition temperature of the polyurethane, synthesised from HMODAz, is −20° C. and the glass transition temperature of polyurethane synthesised from HODEAz is −48° C. It is therefore interesting to ascertain that these polyurethanes have low glass transition temperatures (below ambient temperature). Said polyurethanes can therefore be coupled with other rigid block polymers to prepare thermoplastic elastomers.

Example 6

Synthesis of Polyurethane from Ricinoleic Acid

The AB-type monomer (compound 10 hereunder) was prepared following the reaction scheme described below:

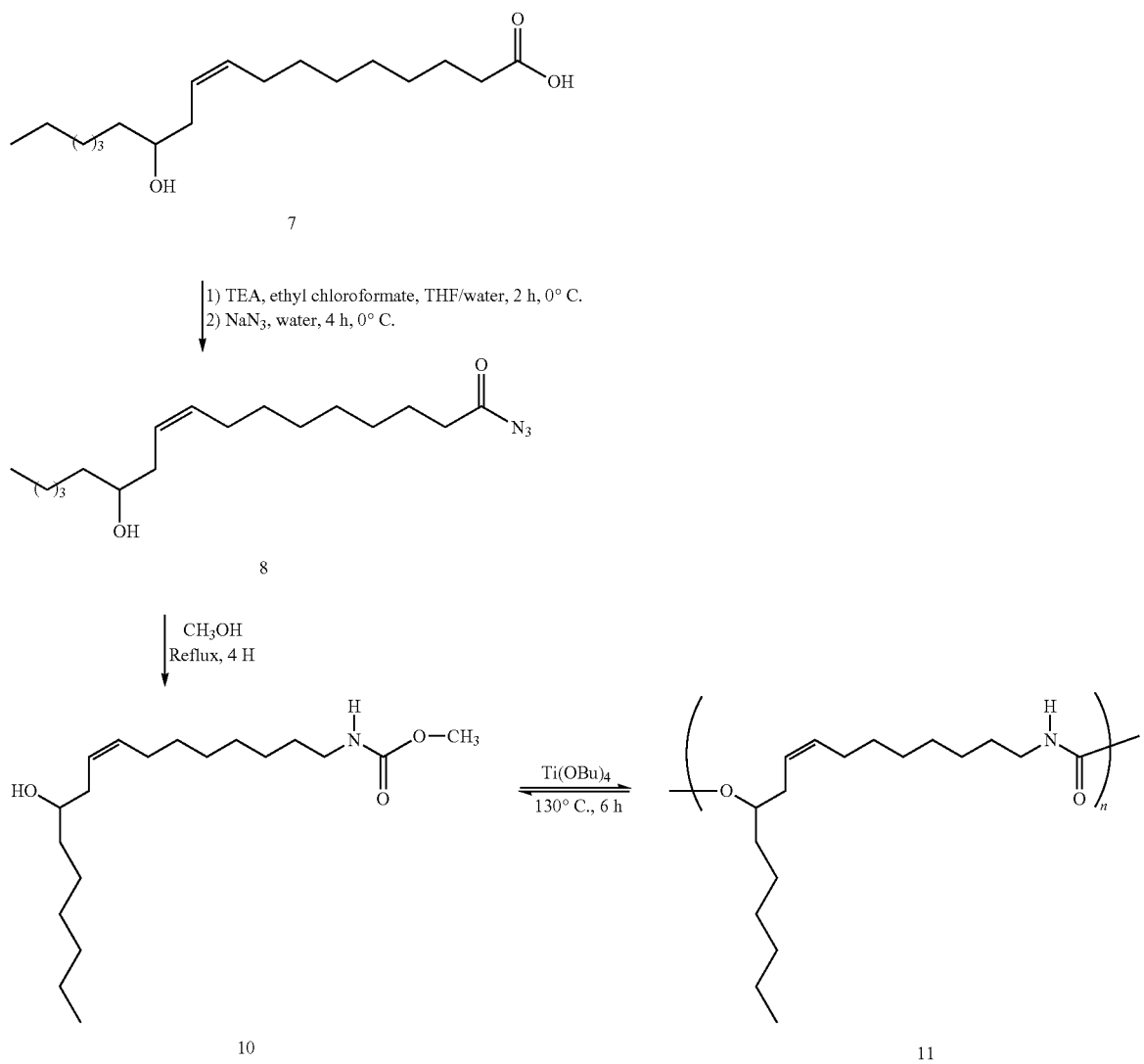

Synthesis of methyl-11-hydroxyheptdec-8-enylcarbamate (10), AB-type monomer for transurethanisation To a 100 mL round-bottomed flask equipped with a magnetic stirrer and a reflux condenser were added the azide of 12-hydroxy-octadec-9-enoyl (8) (2.0 g; 0.006 mol) and dry methanol (50 mL). The reaction mixture was placed under reflux for 4 h then the excess methanol was removed using a rotary evaporator. The crude carbamate product was dissolved in dichloromethane (100 mL), washed with water (2×50 mL), dried over anhydrous sodium sulfate, filtered and the solvent removed to obtain the carbamate (10).

Yield: 1.85 g (92%)

IR: 3600-3400 cm$^{-1}$(OH), 3334 (NH), 3008 (=C—H), 1703 cm$^{-1}$ (CO).

$^1$H-NMR (400 MHz, CDCl$_3$)-0.87 (3H, t, CH$_3$); 1.20-1.70 (methylene protons); 3.14 (2H, CH$_2$—NHCOO—); 3.59 (1H, m, CH—OH; 4.63 (1H, NH—COO); 5.3-5.6 (CH=CH).

Polycondensation (Via Transurethanisation) to Obtain Compound (11)

To a twin-neck round-bottomed flask of 50 ml equipped with a magnetic stirrer, a vacuum adapter and a nitrogen inlet were added methyl-11-hydroxyheptdec-8-enylcarbamate (1.0 g; 0.003 mol) and titanium tetrabutoxide (0.035 g; 1×10$^{-4}$ mol). The reaction mixture was purged with nitrogen and placed in a vacuum twice. The reaction flask was held in an oil bath at 130° C. for 4 hours under nitrogen purging then in a vacuum at 130° C. for 2 hours.

Yield: 0.80 g (80%)

IR: 3338 cm$^{-1}$ (NH), 1695 cm$^{-1}$ (CO), 1526 cm$^{-1}$ (NH deformation), 1230 cm$^{-1}$ (C—N).

$^1$H-NMR (400 MHz, CDCl$_3$): 0.86 (CH$_3$); 1.20-1.70 (methylene protons); 3.13 (—CH$_2$—NHCOO); 3.63 (OCH$_3$); 4.86 (NH); 5.3-5.6 (CH=CH).

Transurethanisation is a non-isocyanate route and solvent-free used for the synthesis of polyurethanes. It comprises condensation between bisurethanes (A-A) and diols (B-B) in the presence of a catalyst. However, another route consists of using the method of the invention, namely condensation of an AB-type monomer in the presence of a catalyst, the said monomer being compound (10): methyl-11-hydroxyheptdec-8-enylcarbamate (10).

Figure 5:
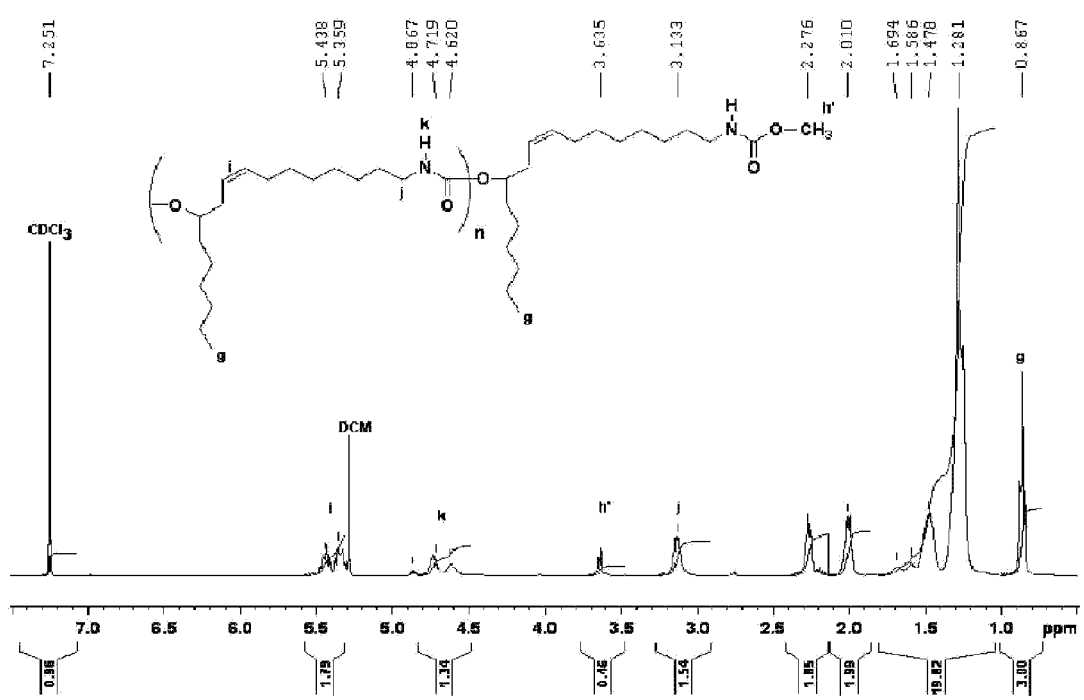
FIG. 5 shows the NMR spectrum of the ($^1$H-RMN) proton of the polyurethane derived from ricinoleic acid (11).

Polycondensation by transurethanisation was conducted at 130° C. in the presence of titanium tetrabutoxide as catalyst in two steps. At the first step, the reaction was conducted at 130° C. by stirring under a stream of nitrogen for 4 h to obtain oligomers. Step two was conducted in a vacuum at 130° C. for 2 h for additional condensation of the oligomers. The polymer obtained was characterised by IR, NMR and GC. Table 3 below indicates the reaction conditions and the results of the transurethanisation reaction. The transurethanisation reaction did not allow an increase in molecular weight in the absence of catalyst. The $^1$H-NMR spectrum of the polyurethane (11) confirms the structure of the polyurethane (FIG. 5). The transurethanisation reaction was confirmed on the basis of a decrease in the intensity of the $OCH_3$ protons at 3,65 ppm in comparison with a signal intensity due to the —$CH_2NHCOO$— protons at 3.13 ppm. At the reaction temperature, the presence of a double bond in the polymer suggests that there are not any secondary reactions due to the double bond.

TABLE 3

Experimental conditions and transurethanisation results (compound 11)

| Test | Catalyst | Temperature (°C.) | TIME (h) | $M_n$ | SEC[b] $M_w$ | $M_w/M_n$ |
|---|---|---|---|---|---|---|
| 1 | $(Ti(OBu)_4$ | 130 | 6 | 6950 | 9850 | 1.41 |
| 2[c] | none | 130 | 6 | — | — | — |

[b]based on PS calibration;
[c]no polymer

The invention claimed is:
1. A compound of following formula (I):

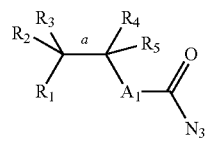

(I)

in which:
R$_1$ is a straight-chain or branched alkyl group comprising 1 to 20 carbon atoms, optionally substituted by one or more OR$_a$ substituents, R$_a$ representing a hydrogen atom or an alkyl group comprising 1 to 20 carbon atoms, the said group R$_1$ optionally containing one or more unsaturations;
a represents a single or double bond;
R$_2$ is a hydrogen atom, an OR$_a$ group, R$_a$ representing a hydrogen atom or an alkyl group comprising 1 to 20 carbon atoms, or a straight-chain or branched alkyl group comprising 1 to 20 carbon atoms substituted by an OH group,
or R$_2$ is a radical of formula —(OCH$_2$CH$_2$)$_n$—OH or —CH$_2$(CH$_2$OCH$_2$)$_n$—CH$_3$, n representing an integer of 1 to 100;
R$_3$, when a is single bond, represents a hydrogen atom or, when a is a double bond, R$_3$ is absent;
R$_4$ is a hydrogen atom or an OR$_b$ group, R$_b$ representing a hydrogen atom or an alkyl group comprising 1 to 20 carbon atoms, or a straight-chain or branched alkyl group comprising 1 to 20 carbon atoms substituted by an OH group,
or R$_4$ is a radical of formula —(OCH$_2$CH$_2$)$_n$—OH or —CH$_2$—(CH$_2$OCH$_2$)$_n$—CH$_3$, n representing an integer of 1 to 100;
R$_5$, when a is a single bond, represents a hydrogen atom, or when a is a double bond R$_5$ is absent; and
A$_1$ is a divalent alkylene radical, straight-chain or branched, comprising 1 to 20 carbon atoms, the said alkylene radical optionally containing one or more unsaturations,
wherein at least one of the groups R$_1$, R$_2$ and R$_4$ comprises an OH group.
2. The compound according to claim 1, wherein, when R$_2$ is a radical of formula —(OCH$_2$CH$_2$)$_n$—OH or —CH$_2$—(CH$_2$OCH$_2$)$_n$—CH$_3$, then n is an integer of 6 to 50.
3. The compound according to claim 2, wherein, when R$_2$ is a radical of formula —(OCH$_2$CH$_2$)$_n$—OH or —CH$_2$—(CH$_2$OCH$_2$)$_n$—CH$_3$, then n is an integer of 6, 13 or 45.
4. The compound of formula (I) according to claim 1 wherein, when a represents a single bond, at least one of the groups R$_2$ and R$_4$ comprises an OH group.
5. The compound according to claim 1 of the following formula (1-2):

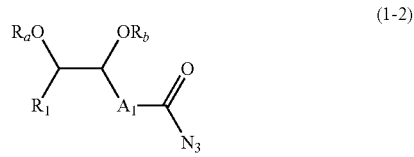

(1-2)

where:
R$_1$ is a straight-chain or branched alkyl group comprising 6 to 12 carbon atoms,
R$_a$ is a hydrogen atom or an alkyl group comprising 1 to 12 carbon atoms,
R$_b$ is a hydrogen atom or an alkyl group comprising 1 to 12 carbon atoms, and
A$_1$ is a divalent alkylene radical, straight-chain or branched, comprising 6 to 12 carbon atoms.
6. The compound according to claim 1 of the following formula (1-3):

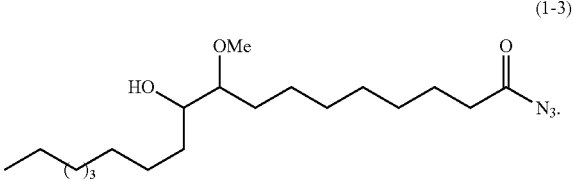

(1-3)

7. The compound according to claim 1 of the following formula (1-5):

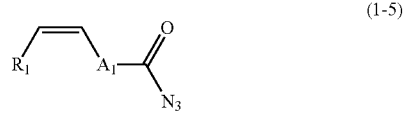

(1-5)

where:
R$_1$ is a straight-chain or branched alkyl group comprising 6 to 12 carbon atoms, substituted by an OH group;
A$_1$ is a divalent alkylene radical, straight-chain or branched, comprising 6 to 12 carbon atoms.

8. The compound according to claim 7 of the following formula (1-7):

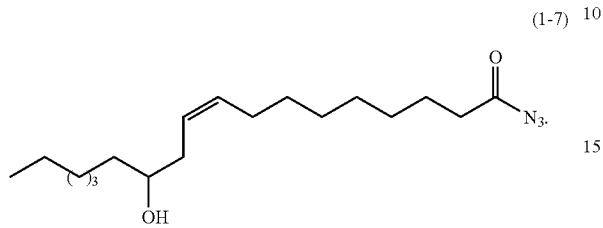

(1-7)

9. A method for preparing a compound of formula (I) according to claim 1, comprising reacting a compound of the following formula (II):

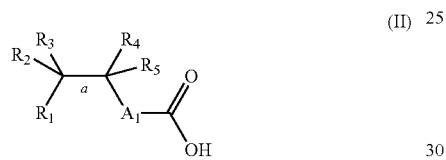

(II)

where R$_1$, R$_2$, R$_3$, Ra, R$_5$, A$_1$ and a, are such as defined in claim 1, with ethyl chloroformate in the presence of triethylamine, then with sodium azide.

10. Method for preparing polyurethane, comprising self-condensing a compound of formula (I) according to claim 1.

11. A method for preparing polyurethane meeting the following formula (III-I):

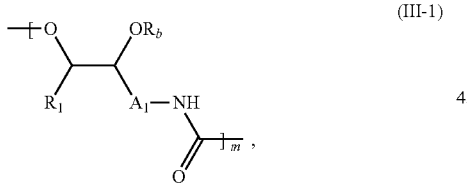

(III-1)

wherein:
A$_1$ is a divalent alkylene radical, straight-chain or branched, comprising 6 to 12 carbon atoms;
R$_1$ is a straight-chain or branched alkyl group comprising 6 to 12 carbon atoms; and
R$_b$ is a hydrogen atom or an alkyl group comprising 1 to 12 carbon atoms; and
m representing an integer of 2 to 50000;
comprising self-condensing a compound according to claim 5.

12. A method for preparing polyurethane, comprising self-condensing a compound according to claim 1 at a temperature of between 50° C. to 100° C., for a time of 1 hour to 48 hours.

13. The method according to claim 12, wherein the temperature is 80° C.

14. The method according to claim 12, wherein the time is of 24 hours.

15. A method for preparing polyurethane, comprising:
reacting a compound according to claim 1 with an alcohol R$_7$OH, R$_7$ representing a straight-chain or branched alkyl group comprising 1 to 4 carbon atoms, to obtain a compound of the following formula (IV):

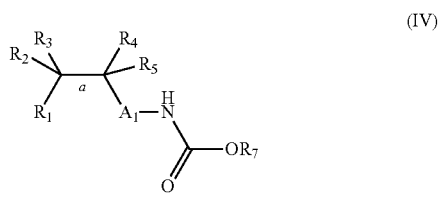

(IV)

where R$_1$, R$_2$, R$_3$, R$_4$, R$_5$, A$_1$ and a, are such as defined in claim 1, and
polycondensing the formula (IV) compound in the presence of titanium tetrabutoxide at a temperature of between 80° C. and 180° C., for a time of 2 hours to 48 hours.

16. The method according to claim 15, wherein R$_7$ is a methyl group.

17. The method according to claim 15, wherein the temperature is 130° C.

18. The method according to claim 15, wherein the time is of 6 hours.

19. A method for preparing polyurethane meeting the following formula (III-1-1):

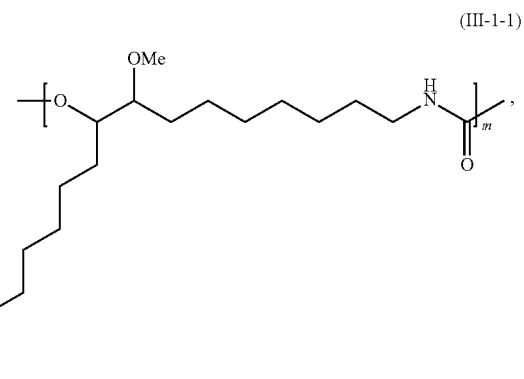

(III-1-1)

m representing an integer of 2 to 50 000;
comprising self-condensing a compound according to claim 6.

20. A method for preparing polyurethane meeting the following formula (III-2-1):

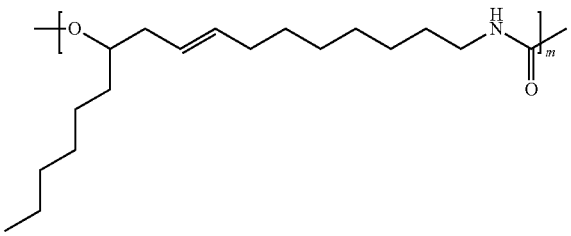

m representing an integer of 2 to 50 000;
comprising self-condensing a compound according to claim 8.

21. A method for preparing polyurethane meeting the following formula (III-3-1):
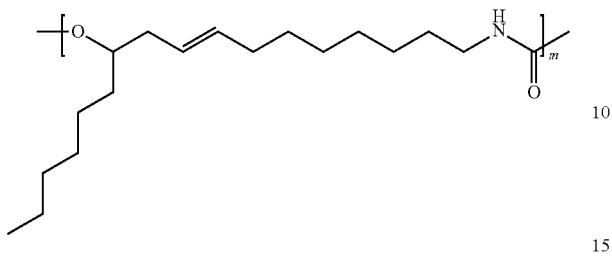
(III-3-1)
m representing an integer of 2 to 50 000;
comprising reacting a compound according to claim 8, with an alcohol $R_7OH$, $R_7$ representing a straight-chain or branched alkyl group comprising 1 to 4 carbon atoms.
* * * * *

UNITED STATES PATENT AND TRADEMARK OFFICE
CERTIFICATE OF CORRECTION

PATENT NO. : 9,133,305 B2
APPLICATION NO. : 13/502284
DATED : September 15, 2015
INVENTOR(S) : Henri Cramail It is certified that error appears in the above-identified patent and that said Letters Patent is hereby corrected as shown below:

In The Specification

In column 2 at line 32, Change "ORa" to --$OR_a$--.

In column 4 at line 9 (approx.), Change "R1" to --$R_1$--.

In column 4 at line 14 (approx.), Change "R2" to --$R_2$--.

In column 5 at line 35 (approx.), Change "ORb" to --$OR_b$--.

In column 8 at line 17, Change "50 000," to --50000,--.

In column 8 at lines 17-18, Change "to10 000," to --to 10000,--.

In column 8 at line 18, Change "5 000" to --5000--.

In column 8 at line 43, Change "50 000," to --50000,--.

In column 8 at lines 43-44, Change "to10 000," to --to 10000,--.

In column 8 at line 44, Change "5 000" to --5000--.

In column 8 at line 61, Change "50 000," to --50000,--.

In column 8 at lines 61-62, Change "10 000," to --10000,--.

In column 8 at line 62, Change "5 000" to --5000--.

In column 9 at line 14, Change "50 000," to --50000,--.

In column 9 at lines 14-15, Change "10 000," to --10000,--.

In column 9 at line 15, Change "5 000," to --5000,--.

In column 9 at line 33 (approx.), Change "50 000," to --50000,--.

In column 9 at lines 33-34 (approx.), Change "10 000," to --10000,--.

In column 9 at line 34 (approx.), Change "5 000" to --5000--.

In column 9 at line 58, Change "50 000," to --50000,--.

In column 9 at lines 58-59, Change "10 000," to --10000,--.

In column 9 at line 59, Change "5 000" to --5000--.

Signed and Sealed this
Fourteenth Day of June, 2016

Michelle K. Lee
*Director of the United States Patent and Trademark Office*

In column 9 at line 62, Change "(111-2-1)," to --(III-2-1),--.

In column 11 at line 43, Change "transesterfied" to --transesterified--.

In column 14 at line 56, Change "($CON_S$);" to --($CON_3$);--.

In The Claims

In column 20 at line 26, In Claim 5, change "(1-2):" to --(I-2):--.

In column 20 at line 29 (approx.), In Claim 5, change "(1-2)" to --(I-2)--.

In column 20 at line 46, In Claim 6, change "(1-3):" to --(I-3):--.

In column 20 at line 49 (approx.), In Claim 6, change "(1-3)" to --(I-3)--.

In column 20 at line 59, In Claim 7, change "(1-5):" to --(I-5):--.

In column 20 at line 61 (approx.), In Claim 7, change "(1-5)" to --(I-5)--.

In column 21 at line 7, In Claim 8, change "(1-7):" to --(I-7):--.

In column 21 at line 10, In Claim 8, change "(1-7)" to --(I-7)--.

In column 21 at line 33, In Claim 9, change "Ra," to --$R_4$,--.

In column 22 at line 48, In Claim 19, change "50 000;" to --50000;--.

In column 22 at line 65, In Claim 20, change "50 000;" to --50000;--.

In column 23 at line 17 (approx.), In Claim 21, change "50 000;" to --50000;--.